(12) United States Patent
Kang et al.

(10) Patent No.: US 7,580,505 B2
(45) Date of Patent: *Aug. 25, 2009

(54) METHOD FOR INSPECTING OBJECT USING MULTI-ENERGY RADIATIONS AND APPARATUS THEREOF

(75) Inventors: Kejun Kang, Beijing (CN); Haifeng Hu, Beijing (CN); Zhiqiang Chen, Beijing (CN); Yuanjing Li, Beijing (CN); Xuewu Wang, Beijing (CN); Chuanxiang Tang, Beijing (CN); Liming Wang, Beijing (CN); Yinong Liu, Beijing (CN); Yaohong Liu, Beijing (CN); Li Zhang, Beijing (CN); Jianmin Li, Beijing (CN); Huaqiang Zhong, Beijing (CN); Jianping Cheng, Beijing (CN); Huaibi Chen, Beijing (CN); Hua Peng, Beijing (CN); Yali Xie, Beijing (CN); Junli Li, Beijing (CN); Ning Kang, Beijing (CN); Qinghua Li, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 180 days.

This patent is subject to a terminal disclaimer.

(21) Appl. No.: 11/647,558

(22) Filed: Dec. 29, 2006

(65) Prior Publication Data
US 2007/0183568 A1   Aug. 9, 2007

(30) Foreign Application Priority Data
Dec. 31, 2005   (CN) .......................... 2005 1 0136319

(51) Int. Cl.
G01N 23/04  (2006.01)

(52) U.S. Cl. .......................... 378/57; 378/54

(58) Field of Classification Search .................. 378/5, 378/51–57, 98.9, 98.11, 98.12
See application file for complete search history.

(56) References Cited

U.S. PATENT DOCUMENTS

| 5,524,133 | A | 6/1996 | Neale et al. .................. 378/53 |
| 6,018,562 | A | 1/2000 | Willson | |
| 6,069,936 | A | 5/2000 | Bjorkholm ................ 378/98.9 |
| 2006/0291619 | A1* | 12/2006 | Statham ...................... 378/45 |
| 2007/0286329 | A1* | 12/2007 | Wang et al. .................... 378/2 |

FOREIGN PATENT DOCUMENTS

| JP | 3075583(A) | 3/1991 |
| JP | 8178873(A) | 7/1996 |

(Continued)

*Primary Examiner*—Courtney Thomas
(74) *Attorney, Agent, or Firm*—Jacobson Holman PLLC

(57) ABSTRACT

The present invention discloses a method for inspecting an object using multi-energy radiations and an apparatus thereof. The method comprises the steps of: causing multi-energy radiations to interact with an object under inspection; detecting and recording detection values after an interaction between the multi-energy radiations and the object under inspection; substituting a portion of the detection values into a predetermined calibration function to obtain information comprising primary material attribute; and determining further material attributes of the object by applying a set of functions suitable for a energy band corresponding to the information. The present invention is applicable to the large container cargo inspection without opening containers at customs, ports and airports.

36 Claims, 6 Drawing Sheets

FOREIGN PATENT DOCUMENTS

| | | |
|---|---|---|
| KR | 1019960704241 | 6/1999 |
| WO | WO95/20910 | 8/1995 |
| WO | WO9718462(A1) | 5/1997 |
| WO | WO 2004/030162 A2 | 4/2004 |
| WO | WO 2005/084352 A2 | 9/2005 |

* cited by examiner

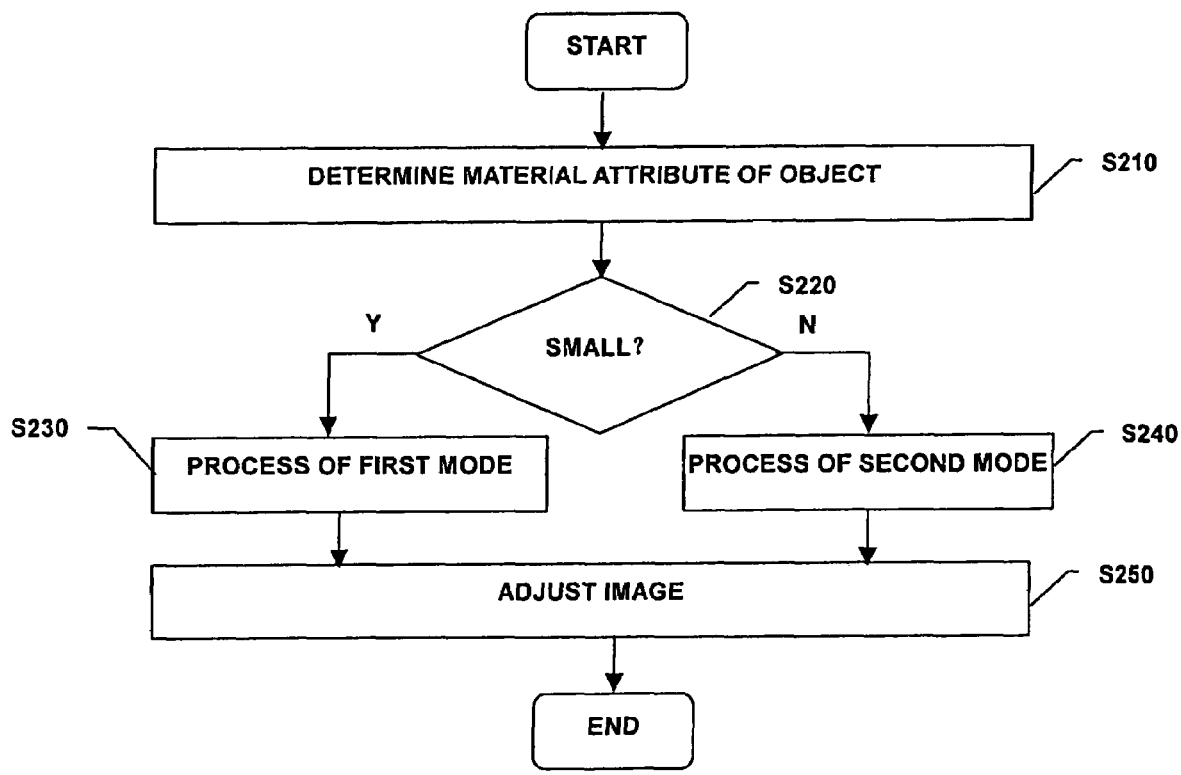

METHOD FOR INSPECTING OBJECT USING MULTI-ENERGY RADIATIONS AND APPARATUS THEREOF

FIELD OF THE INVENTION

The present invention relates to a method for inspecting a large object using multi-energy radiations and an apparatus thereof, more specifically, to a method capable of identifying and imaging materials in a large or medium-sized object, such as cargo or air cargo containers, by utilizing multi-energy ionizing radiation and an apparatus thereof.

BACKGROUND OF THE INVENTION

The commonly used existing cargo inspection system, which employs radiography technology, generally causes a single energy radiations to interact with the inspected object, detects the radiations which have interacted with the inspected object, and then obtains an image. Such a system is capable of reflecting the change in shape and mass thickness of the inspected object. However, it can't identify materials in the object.

It is well known that when X-rays with different energy levels interact with an object, the resultant physical reaction is related to the material attribute of the object. Thus, the interaction between X-rays and the same material varies with the energy change of X-rays. The probability with which photoemission, Compton and electron pair effects would occur predominate respectively in different energy spectra. The three physical effects also correlate to the atomic number of the material.

The specific interaction relationship between X-rays and object is expressed by Equation (1):

$$\mu_m t_m = -\ln\left(\frac{I'}{I_0}\right) \quad (1)$$

where $t_m$ represents mass thickness of the object, $\mu_m$ represents equivalent mass attenuation coefficient of this energy spectrum for X-rays and is related to materials of the object and radiation energy, $I'$ represents the intensity value of X-rays having certain energy after interacting with the object under inspection, and $I_0$ represents the intensity value of the X-rays having certain energy before interacting with the object.

It is obvious that the respective influences from the material and the mass thickness of the object can't be distinguished simultaneously from each other if only using the radiations having a single energy. However, it is possible to obtain the probability that an associated physical reaction has occurred between X-rays having different energy levels and the material by detecting the resultant X-rays after X-rays interacts with the object, and thereby determining the material attribute of the object. In small-sized luggage inspection system, the identification for the material of object under inspection is realized by use of X-rays with two different energy levels. However, the energies of X-rays used in such a system are not sufficient to penetrate through items of large mass thickness at all, and thus this approach is inapplicable to examining large or medium-sized objects, such as containers and air containers.

Several years ago, Patent Document 1 (U.S. Pat. No. 5,524,133) proposed a technical concept that two high-energy X-ray beams with different energy levels are used to recognize the material attribute of large-sized objects. In such a system, two sets of fixed X-ray sources and two corresponding groups of detector arrays are provided. The two X-ray machines provide two X-ray beams with different energy levels, where one of the energy levels is higher than the other. For example, one of the energy levels is 5 MeV and the other is 1 MeV. Then, the average atomic number of the material is determined by looking up a pre-created look-up table based on the ratio between the two detection results. Due to the problems of complex structure, expensive cost, etc. caused by two sets of X-ray machines and two groups of detector arrays, this method has not been widely applied since it is disclosed in 1993.

In order to overcome the problems of complex structure, expensive cost, etc., Patent Document 2 (WO 00/437600) and Patent Document 3 (U.S. Pat. No. 6,069,936) proposed to obtain two X-ray beams by modulating the X-ray beams generated from one accelerator through a filter. Both of technical concepts of Patent Document 2 and Patent Document 3 are to use a single accelerator to obtain X-ray beams having different energy levels. However, the two X-ray beams obtained by filtering the X-ray beams using the filter mounted on the accelerator have limited difference in their energy spectra, thereby restricting the scope for an accurate material identification.

Patent Document 4 (WO 2004/030162 A2) proposed an approach of obtaining dual-energy X-rays based on traveling wave LINAC. It demonstrates the feasibility to obtain two X-ray beams with different energy levels by means of a single accelerator.

Patent Document 5 (WO 2005/084352 A2) discloses that a high and dual-energy method is utilized to detect the object containing high-Z (high atomic number) materials. In Patent Document 5, a statistical function is given, and a threshold is adjusted based on the selected standard variance for balancing sensitivity and accuracy, and further warning of the high-Z material whose atomic number is higher than a preset value.

All of the above-mentioned methods are the material-identifying method by use of radiations having two different energy levels, in which the determination is made as to whether the object is suspect by computing from the detection results on the two different energy levels. In Patent Document 1 and Patent Document 5, the computation is performed in a manner of, for example, looking up a look-up table based on the ratio between the two detection results, so as to determine whether the object contains suspicious material. However, because of the limitation of the energy levels of two X-ray beams and existing detection errors, the chance is very high that a misjudgment occurs in this method when the object to be detected is seriously intermixed, or when the object has a small mass thickness. According to the judging method using the ratio between two detected values, the same function form is unable to distinguish the detected values' difference between different materials, and meanwhile, there exists probability that the ratios between different materials are the same. This will lead to an inaccurate detection result. Moreover, since the material range to which the two energy levels are sensitive is limited, it is impossible to accurately identify both the low and high-Z materials at the same time.

SUMMARY OF THE INVENTION

In view of the above, the present invention was done. An object of the present invention is to provide a method for inspecting object using multi-energy radiations, and an apparatus thereof, in which radiation beams with various energy levels are utilized to interact with the object, and then the interaction result is used to perform a curve fitting computation and analysis, thereby realizing the identification for different materials in a wide range and further the non-destructive inspection on items.

According to an aspect of the invention, there is provided a method for inspecting an object using multi-energy radiations comprising the steps of: causing multi-energy radiations to interact with an object under inspection; detecting and recording detection values after an interaction between the multi-energy radiations and the object under inspection; substituting a portion of the detection values into a predetermined calibration function to obtain information comprising primary material attribute; and determining further material attributes of the object by applying a set of functions suitable for a energy band corresponding to the information.

Preferably, the information further comprises mass thickness information of the object.

Preferably, the calibration function is a fitting function of the detection values obtained after the radiations having different energy levels interact with a known material.

Preferably, the number of radiation beams which have different energy levels and are used for fitting the calibration function and interacting with the known material, is equal to or greater than that of the radiations having different energy levels used for interacting with the materials in the object under inspection.

Preferably, the multi-energy comprises at least three different energy levels or energy spectra.

Preferably, each detection value obtained after the interaction with the object is the transmission intensity obtained after the radiations penetrate the object.

Preferably, each detection value obtained after the interaction with the object is the transmission intensity obtained after the radiations penetrate the object.

Preferably, the energy band is referred as a specific energy band corresponding to certain material, and in the energy band, the detection values as a result of the interaction between the radiations and the materials have a greater difference when compared to the detection values for other materials.

Preferably, the set of functions are referred as functions capable of amplifying the distinction between the detected values of different materials.

Preferably, the set of functions are referred as different function processing models used for segmental processing correspondingly to objects having different mass thickness.

Preferably, the source of the radiations is a radioactive isotope.

Preferably, the source of the radiations is an accelerator.

Preferably, the source of the radiations is an X-ray machine.

According to another aspect of the invention, there is provided a method for inspecting an object using multi-energy radiations comprising the steps of: causing multi-energy radiations to interact with an object under inspection; detecting and recording detection values after the interaction between the multi-energy radiations and the object under inspection, and forming images corresponding to the X-rays having different energy levels; substituting a part of the detection values into a predetermined calibration function to determine the mass thickness of the object; and selecting weighting factors for the detection values based on the mass thickness to combine the images so as to obtain more accurate gray-scale image.

Preferably, the method further comprising a step of converting the gray-scale image into corresponding color levels in color image.

Preferably, the multi-energy comprises at least two different energy levels or energy spectra.

Preferably, determining the mass thickness is based on the actual attenuation of the radiations.

Preferably, selecting weighting factors for the detection values means the smaller the mass thickness is, the smaller the weighting factor for the detection values of high-energy radiations are, and the larger the weighting factors for the detection values of low-energy radiations are; while the lager the mass thickness is, the smaller the weighting factors for the detection values of low-energy radiations are, and the larger the weighting factors for the detection values of high-energy radiations are.

According to still another aspect of the invention, there is provided an apparatus for inspecting an object using multi-energy radiations comprising: a set of radiation source for generating multi-energy radiations; a detector module array adapted to detect simultaneously multi-energy radiations; a processor connected to the detector module array for processing detection values obtained after the interaction between the multi-energy radiations with an object under inspection so as to obtain material attribute and/or produce gray-scale images of the object; and a control system connected to the radiation source for changing operating parameters of the radiation source.

Preferably, the multi-energy comprises at least three different energy levels or energy spectra.

Preferably, the detector module array is a multi-layered multi-crystal detector compounded of different crystals.

Preferably, the different crystals of the detector module array are spaced from each other by filter sheets.

Preferably, the radiation source is a radioactive isotope.

Preferably, radiation source is a combination of the radioactive isotopes of different elements, and the radiations having different energy levels are generated by making the different radioactive isotopes pass through the slots of a collimator in a time series.

Preferably, the radiation source is an accelerator capable of emitting radiations having a continuous energy spectrum in which respective energy levels predominate.

Preferably, accelerator includes an energy spectrum modulator for modulating the energy spectrum in front end of the radiation exit.

Preferably, the radiation source is an X-ray machine.

Preferably, the X-ray machine includes an energy spectrum modulator for modulating the energy spectrum in front end of the radiation exit.

Preferably, the energy spectrum modulator has a shape of a wheel, with vanes formed of different modulation materials and rotating around an axis in the time series corresponding to the radiations having the corresponding energy levels.

Preferably, the energy spectrum modulator synchronizes the beam emission of the radiation source with the signal collection of the detector by transmitting a trigger signal to a control system of the radiation source and a collection signal to a controller of the detector.

Preferably, when receiving the trigger signal, the control system sends immediately to the radiation source the signals corresponding to the different energy levels so that the radiation source operates in the desirable operating states.

Preferably, each detection value of different energy levels is the transmission intensity obtained after the radiations penetrate through the object under inspection.

By using X-rays with different energy levels or energy spectra to identify materials of the object, different optimum energy bands for distinguishing can be employed for respective materials, which can improve the accuracy for material distinguishing to a great extent. Moreover, the combined effect of material attribute and mass thickness of the object tends to cause the intersection of the detected result curves. However, it is beneficial to the improvement of accuracy for material distinguishing that a number of detected values for multi-energy X-rays are employed to fit curves for material identification. In addition, since the functions of the segmental fitting functions obtained from the detected values of the known materials serves as comparison thresholds, the overall determination is based on actual measurement values, and by a secondary determination and the special processing for thickness, the errors due to direct interpolation and looking up a table can be reduced and the accuracy for material identification can be improved.

By obtaining the detection values after X-rays with different energy levels interact with materials, and by assigning different weighting factors to high-energy and low-energy data respectively, clear gray-scale images and color images with rich color levels can also be acquired for materials having a larger difference in mass thickness.

Based on different objects for material discrimination, different modulation materials are utilized to modulate energy spectra for different energy levels of the X-rays generated by the accelerator, thereby gaining an optimum effect of energy spectrum modulation and an optimum energy spectrum for discriminating materials. This decreases errors in the final discrimination results due to the energy spectrum scattering of radiations.

The multi-layered detector is able to further enhance detection effects for radiations with different energy levels, thereby improving detection effects and accuracy.

BRIEF DESCRIPTION OF THE DRAWINGS

FIG. 8 is an overall flowchart of a method for adjusting images by use of the information on different mass thickness.

DETAILED DESCRIPTION OF THE PREFERRED EMBODIMENTS

According to the present invention, during scanning the container cargo, the accelerator is required to generate high-energy X-rays with sufficient energy and amount so that the effective signal can be detected by a detector after X-rays penetrate through the container cargo. In order to discriminate the materials of the inspected object, the key is that the accelerator generates several X-ray beams having different energy levels, and then the X-rays interact with the inspected object at the same position thereon and are accurately detected by the detector.

Figure 1:
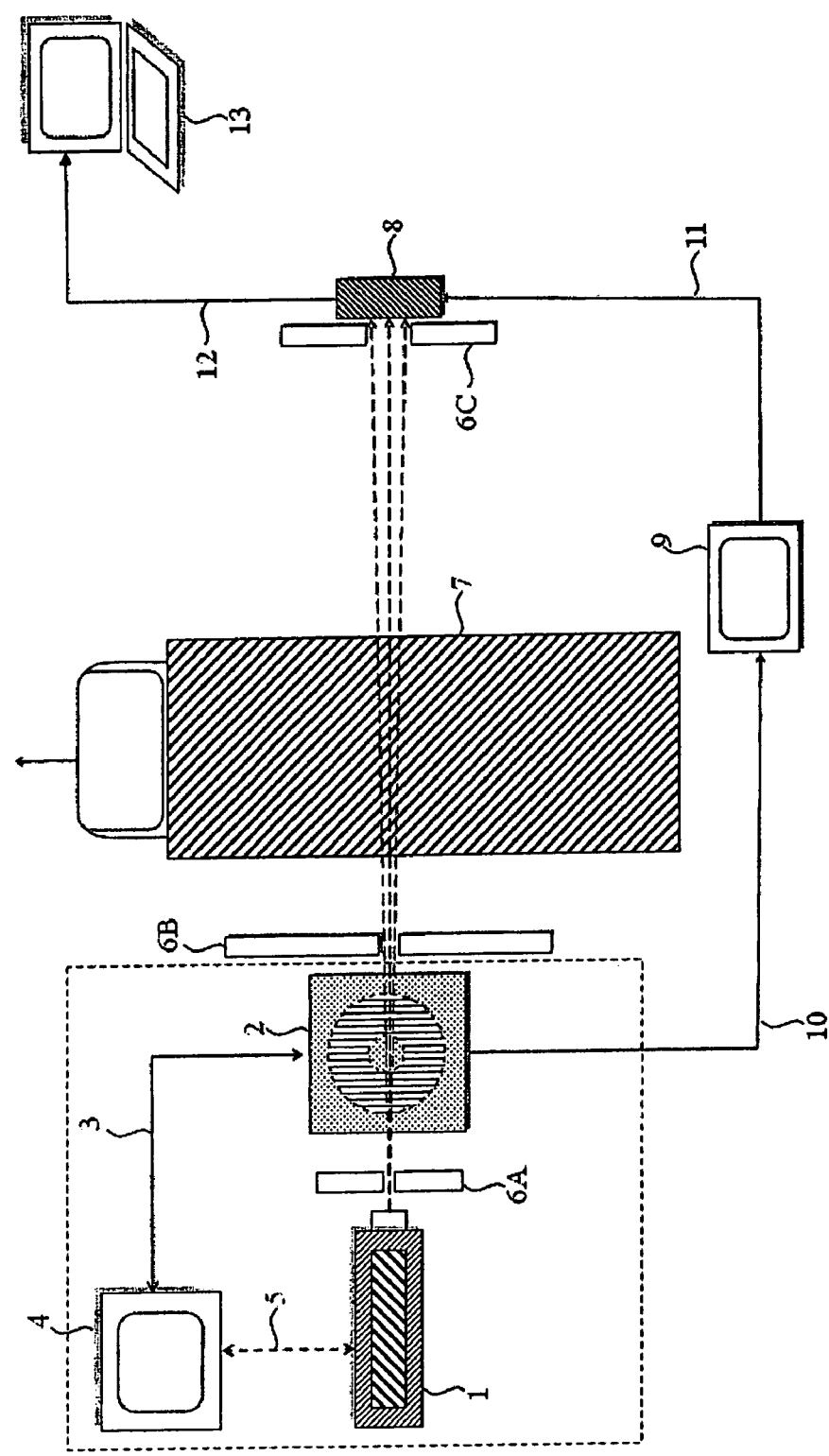
FIG. 1 is a profile diagram of an apparatus for inspecting object using multi-energy radiations according to an embodiment of the present invention.

FIG. 1 is a profile diagram of an apparatus for inspecting object using multi-energy radiations according to an embodiment of the present invention. In FIG. 1, an accelerator 1 can generate X-rays having different energy levels by changing its operating parameters. The operating parameters of the accelerator 1 are changed by a control system 4.

The operating states corresponding to the cases of the accelerator generating different energy levels have been stored in control system 4. When receiving the trigger signal 3, the control system 4 sends immediately to the accelerator 1 the signals corresponding to different energy levels to cause the accelerator 1 operates in the required operating states. The accelerator 1 return a completion instruction to the control system 4 when it completes the generation of X-rays with specific energy levels in the required operating states. The X-rays generated by the accelerator 1 are then modulated through the energy spectrum modulator 2, and optimized X-rays are obtained. The several multi-energy X-ray beams interact with at the same position in the inspected object 7. The detector 8 is controlled by the controller 9 to detect the X-rays after the X-rays penetrate through the inspected object 7. The detection signals 12 from the detector 8 are transferred to the workstation 13 over a network. At the workstation 13, the acquired data is processed to obtain the gray-scale images and material attribute of the inspected object.

The X-rays are generated by the accelerated electron beams hitting a target, and then pass through the collimation system 6A to form fan-shaped X-ray beams. In addition, the collimators 6B and 6C shown in the FIG. 1 suppress the scattering radiation during the measurement process.

In the embodiment of the invention, since different materials are utilized to modulate energy spectra with respect to multi-energy X-rays, the trigger signals 3 and 10 are generated via the energy spectrum modulator 2 to realize the synchronization between the beam emission of the accelerator and the data collection of the detector.

Figure 2:
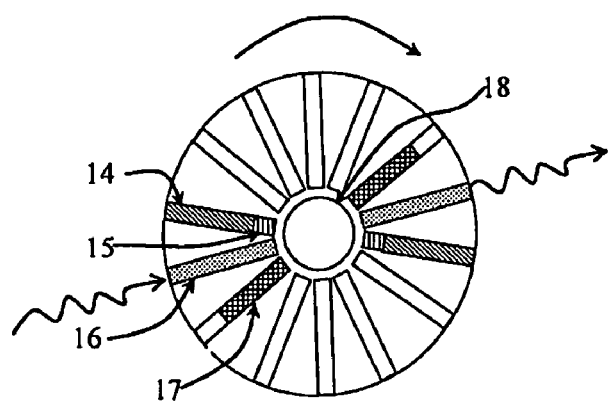
FIG. 2 is a top view of an energy spectrum modulator for modulating multi-energy radiations according to an embodiment of the present invention.

The energy spectrum modulator 2 utilizes different materials of energy spectrum modulation for different energy levels based on the X-rays generated by the accelerator 1. As shown in FIG. 2, the modulator 2 has a shape of wheel, with its axis being a mesh-shaped hollow axis. The vanes, which are rotatable around the axis, are made of different modulation materials. The trigger signals can be sent to the controller of the accelerator. Multi-energy X-rays are modulated by respective vanes made of different energy-modulation materials. The interaction between the X-rays and the object is related to not only the X-rays' characteristics but also the object's attribute. As a result, different modulation methods and different-energy X-rays will lead to completely different modulation effects.

For example, since low-Z materials absorb significantly the X-rays having higher energy in energy spectra, when the energy band in the energy spectrum distribution of the X-rays has a lower limit which is higher than some threshold of high energy (for example, ~3 MeV), low-Z materials, such as B, polyethylene and other hydrogen-rich organic materials, should be selected as the energy spectrum modulation material for this X-ray beam.

Since high-Z materials absorb significantly the X-rays having several hundred KeV energy, when the energy band in the energy spectrum distribution of the X-rays has a lower limit which is higher than some threshold of low energy (for example, ~300 KeV), high-Z materials, such as Pb, W, U etc., should be selected as the energy spectrum modulation material for this X-ray beam.

FIG. 2 is a top view of an energy spectrum modulator for modulating multi-energy radiations according to an embodiment of the present invention. As for the X-rays having energy (i. e. energy level) of 3~6 MeV generated by the accelerator 1, and each of the first type vanes used for modulation consist of the first portion 14 and second portion 15. The modulation material of the first portion 14 can be selected as polyethylene and absorb X-rays with higher energy, while that of the second portion 15 can be selected as Pb and absorb scattering component with lower energy.

For X-rays having energy of ~9 MeV, macromolecule materials can be selected to form the second type vanes 16 used for modulation. For X-rays having energy of 200 KeV~1 MeV, the modulation material W can be selected for the third type vanes 17. As shown in FIG. 2, the three types of vanes are arranged around the axis periodically so that X-rays having respective energy levels can be modulated every a predetermined angle.

Figure 3:
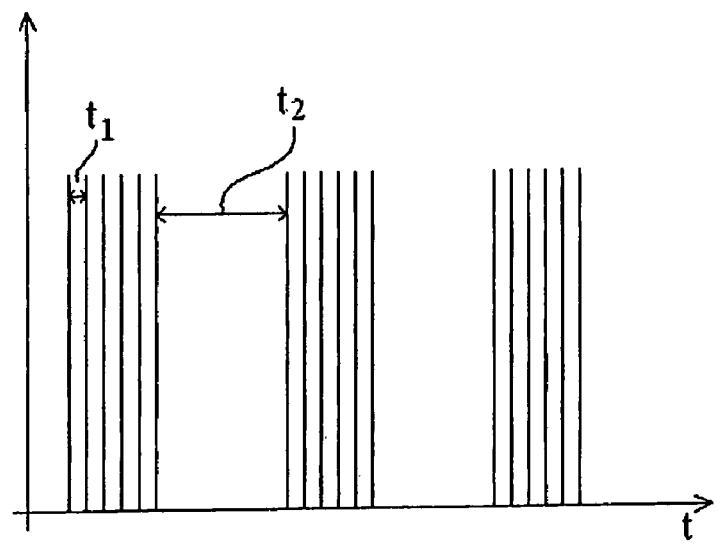
FIG. 3 is a timing chart of the signals sent from the energy spectrum modulator to the control system.

The modulation vanes of the energy spectrum modulator rotate regularly around the axis 18. When one of the modulation vanes of the first type rotate to a stationary position in front of the X-ray plane, a signal is triggered as shown in the timing of FIG. 3. The accelerator 1 continuously generates several X-ray beams having different energy levels, with each beam emitted at an interval $t_1$. The energy spectrum modulator just rotates the next vane to the stationary position when the interval $t_1$ elapses. Then, after the time $t_2$ elapse, the modulation vane of the first type rotates to the same stationary position, triggers a signal again and generates the emission cycle for the next X-ray beam of continuous pulse. Meanwhile, the triggered signal is also sent to the control system of the detector. The detector is caused to start signal collection after certain time delay. Thus, the synchronization in time between every parts of the device is achieved.

Figure 4:
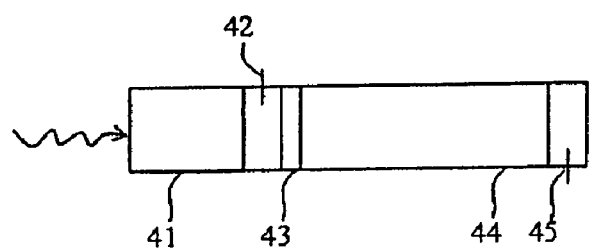
FIG. 4 is a schematic diagram of a detector for implementing an accurate detection of multi-energy radiations according to an embodiment of the present invention.

The detector is a detector with a multi-layered and multi-crystal structure. In this case, the accelerator 1 can be replaced with radioactive isotope. For example, the radiation source is a combination of radioactive isotopes of different elements, and the radiation beams having different energy levels are generated by making the different radioactive isotopes pass through the narrow slots of a collimator in a time series. As shown in FIG. 4, based on the collective levels of different materials for different energy signals, the first sensing part 41 can be formed of CsI crystal and used to collect lower-energy X-rays, and output signals exit from the first output part 42. The other X-rays having higher energy will travel through the first sensing part 41 and the first output part 42, and reach the filtration part 43. The filtration part 43 is a filter sheet and used for filtering lower-energy X-rays for example caused by Compton scattering. The material of the filtration part 43 can be selected as Pb or W. CWO crystal can be selected as the second sensing part 44 in which almost all high-energy components in the X-rays is deposited. The signals of the second sensing part 44 exit from the second output part 45. The detection signals obtained by the detector are converted into 16-bit binary data by an ADC and transferred to the processing workstation 13.

Figure 5:
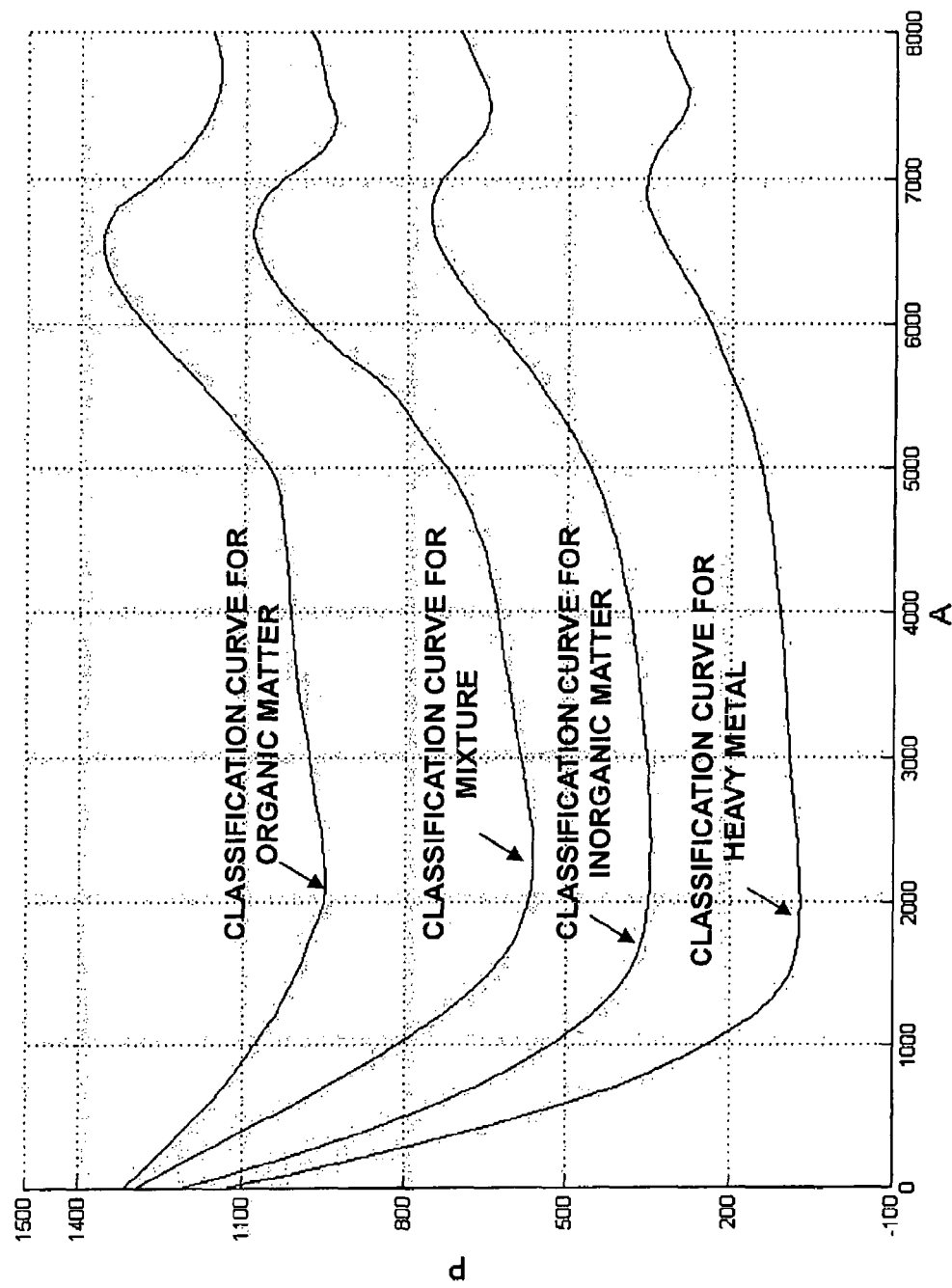
FIG. 5 shows given function curves of the relation between radiation energy levels and the attribute and mass thickness of materials within the entire energy band.

An image processing module is employed to analyze the data after obtaining the detection values. First, a set of functions within all energy bands are calibrated based on the detection results of known materials to form relation curves representing the relation between functions of the sets of functions. As shown in FIG. 5, the functions in the set of functions can be selected as any function. For example, x-coordinate and y-coordinate can be calculated by using functions as Equations (2) and (3):

$$A = \mu_n \times t = \alpha \times |\ln(I_n/I_{n0})| \tag{2}$$

$$P = |(\beta\mu_m - \gamma\mu_n + \eta\mu_k)t| \text{ or } P = |\lambda(\mu_m \times \mu_n)t| \tag{3}$$

where subscripts m, n, and k represent the different energy levels of X-rays, the symbols $\alpha$, $\beta$, $\gamma$, $\eta$ and $\lambda$ are predetermined parameters for known material, and t represents mass thickness of the object, $\mu$ represents a mass attenuation coefficient, $I_n$ represents the values detected after X-rays having $n_{th}$ energy interact with the object, and $I_{n0}$ represents the values detected before X-rays having nth energy interact with the object. The resolutions between different functions in a set of functions vary with the different energy bands. This feature will be used to discriminate different materials by means of functions calibrated for different materials.

During inspection, the detection values of several energy levels for the inspected object are substituted into the calibrated functions, and the resultant function values are compared with the calibrated function values for the known materials, thereby making a primary determination as to the potential material range the inspected object belongs to.

Figure 6:
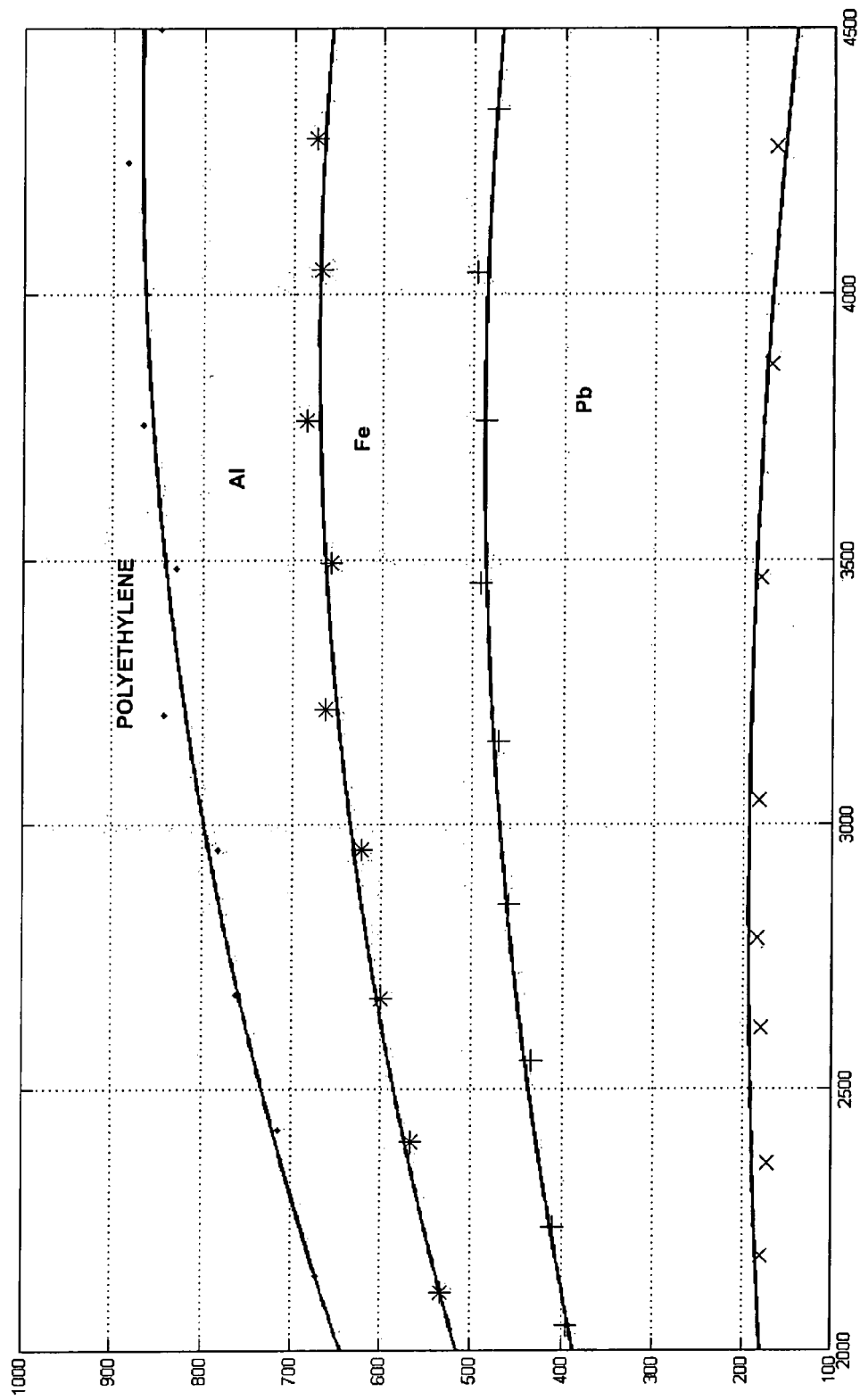
FIG. 6 shows given function curves, which are different from that in FIG. 5, of the relation between radiation energy levels and the attribute and mass thickness of materials within the energy band which is beneficial to distinguish high-Z materials.

The optimum discrimination energy band varies with different materials, and accordingly the function models selected for each of the energy bands are different from one another. As shown in FIG. 6 that illustrates the function relation curves corresponding to the energy band suitable for distinguishing heavy metals. It is obvious that heavy metals can be easily distinguished by using the particular function curves in this energy band. Thus, based on the first-determined range the material belongs to, appropriate forms of energy combination and the function relations of corresponding segments can be further used to determine the material attribute with a higher accuracy.

If the object has a smaller mass thickness, the accuracy for identifying the material of the object will be affected. The object can be considered as having a smaller mass thickness when the function values of the selected function relation fall into certain region of the coordinate, or when the attenuation is very small. In the case that the statistical fluctuation is high for the detection results of the interaction between radiation and an object having a smaller mass thickness, a function relation corresponding to the object having a smaller mass thickness is adopted for further processing the detection values, thereby ensuring the identification accuracy.

For example, for an object having a larger mass thickness, the function expressed in Equation (4) can be selected:

$$P = \alpha \times \ln\left(\frac{I_m}{I_{m0}}\right) - \beta \times \ln\left(\frac{I_n}{I_{n0}}\right) \tag{4}$$

For an object having a smaller mass thickness, the function expressed in Equation (4) is not suitable. In this case, the function expressed in Equation (5) is selected:

$$P = \left(\alpha \times \ln\left(\frac{I_m}{I_{m0}}\right) - \beta \times \ln\left(\frac{I_n}{I_{n0}}\right)\right) \times (\ln(I_m + I_n)) \times \gamma \tag{5}$$

where $I_n$, $I_m$ represent the values detected after X-rays interact with the object; $I_{n0}$, $I_{m0}$ represent the values detected before X-rays interact with the object; $\alpha$, $\beta$, $\gamma$ represent predetermined parameters.

Figure 7:
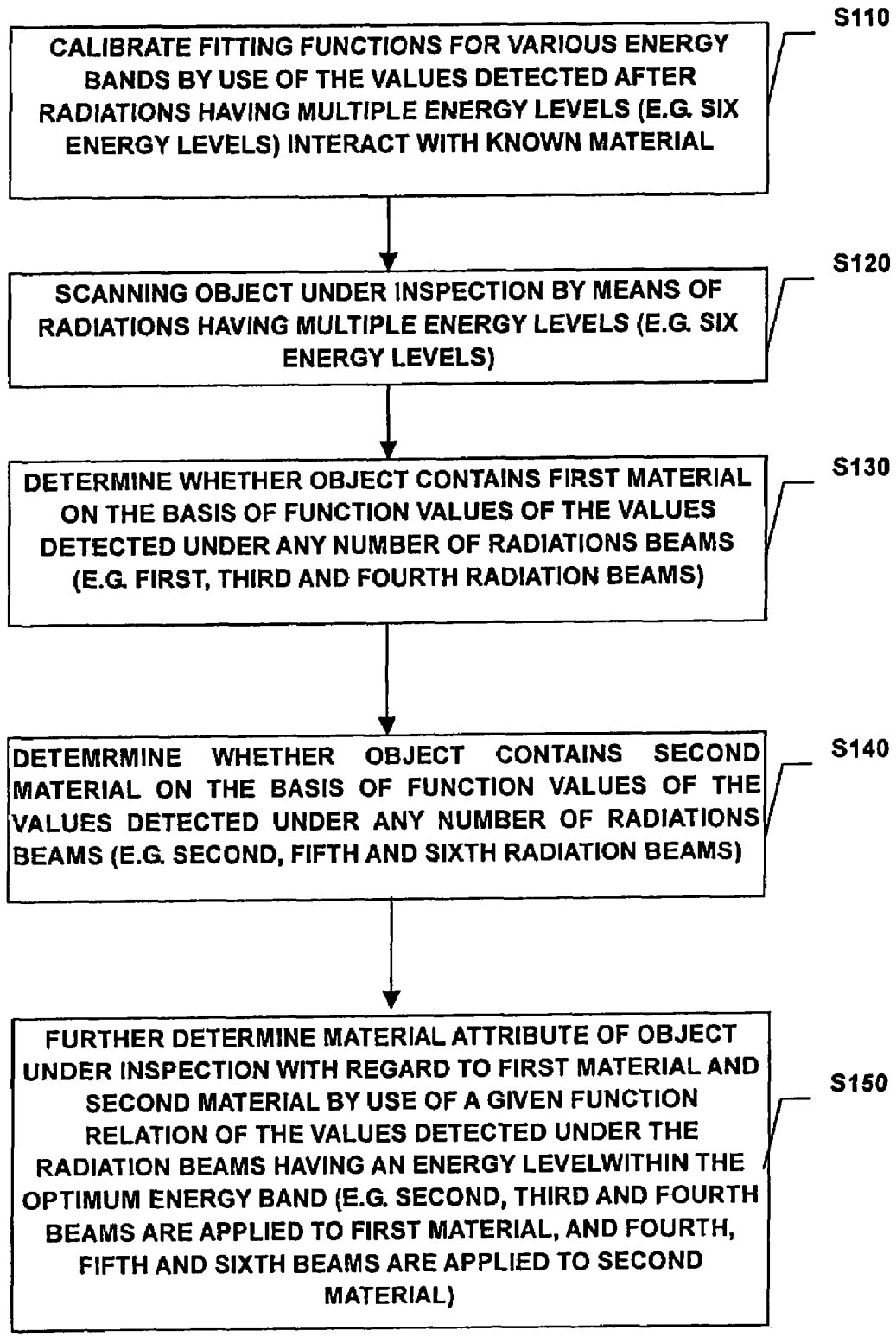
FIG. 7 is an overall flowchart of the process in which the detection values of several radiation beams having different energy levels are used to implement material discrimination.

FIG. 7 shows a flowchart of a method for determining the material attribute with multi-energy X-rays by example of six different energy levels.

At step S110, from the interactions between X-rays having six energy levels and a known material, certain function relation of any three (here the number of X-rays is equal to or more than two and less than six, such as two or four) energy levels of the six is given for function fitting so that the material under inspection is calibrated.

At step S120, the object under inspection is scanned using X-rays having six energy levels. The detector collects the detection values after the object interacting with X-rays having six energy levels. Then, at step S130, the X-rays are classified into two groups on the basis of the energy level thereof. For example, the X-ray having first energy level, the X-ray having third energy level and the X-ray having fourth energy level are classified into the first group. The X-ray having second energy level, the X-ray having fifth energy level and the X-ray having sixth energy level are classified into the second group. At step S130 and S140, the detection values of three energy levels in each group are substituted into the above-described calibration function to determine primarily the attribute of the material. For example, the detection values of the X-rays in the first group can be used to determine whether the object contains the first material, the detection values of the X-rays in the first group can be used to determine whether the object contains the second material.

At step S150, if the determination results by X-rays in the two groups can be Cu and W, respectively, the detection values of energy bands which are more suitable for Cu and W are chosen respectively, and also function relations suitable for the energy bands are used to further determine the attribute material. For example, for the first material, the sets of functions of detection values of X-rays within the optimum energy range, such as the X-rays having the second energy level, the X-rays having the third energy level and the X-rays having the fourth energy level, are employed to further discriminate the material attribute. For the second material, the sets of functions of detection values of X-rays within the optimum energy range, such as the X-rays having the fourth energy level, the X-rays having the fifth energy level and the X-rays having the sixth energy level, are employed to further discriminate the material attribute.

The further discrimination may gain a determination result that one of Cu and W isn't suitable for associated function relation. It is apparent that further increasing energy levels can make the domains more finely divided. It can be seen from the comparison that the method of selecting energy ranges by use of multiple energy levels can greatly improve the determination accuracy for discriminating the material attribute.

Finally, in order to obtain clear image of the object, several images obtained by scanning the object with X-rays having different energy levels can be combined together to generate resultant image having high quality.

As it is well known, the high energy X-rays have more capability to penetrate through the object and the detection values obtained by penetrating through the object having a large mass thickness is more accurate. Therefore, the gray-scale image of the object having a large mass thickness is clearer. However, in the case of high energy X-rays penetrate through the object having a small mass thickness, a blur image lack of more details will be generated. However, such a drawback can just be remedied by the gray-scale image obtained by penetrating through the object with low energy X-rays.

FIG. 8 is an overall flowchart of a method for adjusting images by use of the information on different mass thickness. The image merging process shown in FIG. 8 can combine together the values detected under different to generate a clear image in a broad range of mass thickness.

At steps S210 and S220, the material attribute of the object is determined. For example, it is determined whether the mass thickness of object is large or small. Here, on the basis of the attenuation degree, the mass thickness of object can be determined approximately. If the attenuation is serious, for example it is less than a preset threshold value, the object is considered as having a large mass thickness. If the attenuation is little, for example it is larger than the preset threshold value, the object is considered as having a small mass thickness.

At step S230, for the material having a small mass thickness, a small weighting factor such as 30% is assigned to the detection values obtained under high energy, and a larger weighting factor such as 70% is assigned to the detection values obtained under low energy.

At step S240, for the object having a larger mass thickness, a larger weighting factor such as 70% is assigned to the detection values obtained under high energy, and a smaller weighting factor such as 30% is assigned to the detection values obtained under low energy.

Then, at step S250, a high energy image and a low energy image are combined together in accordance with the weighting factors to get a resultant image which has a higher quality.

As described above, the present invention compares the detection values obtained after the multi-energy X-rays interacting with the materials in the object with the preset threshold values, assign respective weighting factors to high energy values and low energy values in accordance with the comparison results, and get a resultant gray-scale image.

Therefore, although the images detected from the X-rays having different energy levels has different image features, the method of the present invention can get a resultant image with high quality particular for the object having mass thickness very different from each other. In addition, the gray-scale image can be converted into color image on the basis of correspondence between gray-scales and color levels. As such, the clear gray images and color images with rich color levels can be obtained for the object in which each portion has larger difference in mass thickness from each other.

As described above, an accelerator generates at least three X-ray beams with different energy levels, which subsequently interact with the same object, respectively. A detector detects the X-ray that has penetrated through the object, and the detection result is analyzed and processed to achieve the discrimination in the material attribute of the inspected object.

The accelerator can generate the spectra of several X-ray beams, over which different energy proportions predominate, by changing the operating parameters thereof. Since the energy of X-rays generated by the accelerator has a relatively wide spectrum, and the proportion occupied by X-rays with other energy is relatively high, there is need for increase the proportion of the X-rays with required energy in the X-ray spectrum by means of energy spectrum modulation. For X-rays with different energy levels, different materials are used for modulation to obtain optimized X-rays. Indeed, using different radioactive elements as the radiation source of different energy levels doesn't require the energy spectrum modulation. However, the selectable energy spectrum is not continuous.

As described previously, since the X-rays generated by the accelerator is a continuous spectrum, the accuracy for discriminating material will be effected. The present invention employs an energy spectrum modulator to modulate the X-rays generated by the accelerator. Different modulation materials are utilized to perform the energy spectrum modulation for different energy levels, thereby obtaining the energy spectrum most suitable for discriminating materials.

Furthermore, the present invention points out that the distributed energy band in the X-rays energy spectrum is different, and the appropriate material for modulating the energy spectrum is also different. For example, when the major energy band in the energy spectrum distribution of certain X-ray beam has a lower limit which is higher than some threshold of high energy (for example, ~3 MeV), low-Z material, such as boron (B), polyethylene and other hydrogen-rich organic materials, should be selected as the energy spectrum modulation material for this X-ray beam. Meanwhile, in order to absorb the lower energy scattering component in the X-rays, it is preferable to add thin high-Z material for energy spectrum modulation after the energy spectrum modulation of thick high-Z material. When the major energy band in the energy spectrum distribution of certain X-ray beam has a lower limit which is higher than some threshold of low energy (for example, ~300 KeV), high-Z material, such as plumbum (Pb), tungsten (W), uranium (U) etc., should be selected as the energy spectrum modulation material for this X-ray beam. Medium-Z materials, for example, copper (Cu), can also be used.

In the detection part of the present invention, with respect to multi-energy X-ray beams, a detector module is employed to acquire precisely the signal values after the interactions between the multi-energy rays and the materials so as to accurately discriminate the difference between the interactions of the multi-energy X-rays and the object. Different detection crystals sensitive to the X-rays having different energy levels demonstrate different responsive characteristics. The X-rays with different energy levels are caused to generate signals in different detection crystals, and then these signals from the detection on different energy levels are collected and comprehensively processed for further use.

Since the most distinct energy band corresponding to the X-rays varies due to the difference between the interactions of different materials and the rays, the present invention points out that in order to obtain the accurate attributes of different materials, a specific energy band conducive to the material discrimination should be used, with the lowest and the highest thresholds given in advance. For instance, the present invention gives that the energy band most suitable for distinguishing organic and inorganic materials is 0.3 MeV~3 MeV, and the most suitable domain for distinguishing heavy metals is 1 MeV~4 MeV. The processing functions adopted in the present invention are also varies with different energy bands.

The key to discriminate the material attribute by use of X-rays with different energy levels is that the distinctions from the interactions between X-rays with different energy levels and objects is able to be detected accurately. In aforedescribed steps, analysis is also made as to whether the object has a smaller mass thickness. Since the selected detection energy is usually higher than certain value, it is defined that the associated μ can't be too small. Thus, it is possible to determine whether the object has a smaller mass thickness based on the coordinate domain in which the function value is located. When the mass thickness of the inspected object is small, the intrinsic statistical characteristics in radiation physics can't be negligible. Moreover, in the continuous spectrum X-rays generated by the accelerator, it is difficult for the characteristics of the interaction between the X-rays having the predominant energy band and the object to occur. This leads to the deterioration of detection accuracy and the accuracy for recognizing material attributes. In the present invention, the energy band most sensitive to the interaction with the object is selected in the case of the inspected object having a small mass thickness, and then a processing model defined for the great fluctuation phenomenon is utilized to process the detection values correspondingly, and finally the material attributes of the inspected object are obtained correctly.

In addition, some modifications can be made within the scope of the invention. For example, an X-machine can be adopted to replace the accelerator as described above. In this case, the energy spectrum modulator of the invention can be mounted at the beam emission end.

What is claimed is:

1. A method for inspecting an object using multi-energy radiations comprising the steps of:
   causing multi-energy radiations to interact with an object under inspection;
   detecting and recording detection values after the interaction between the multi-energy radiations and the object under inspection;
   substituting a portion of the detection values into a predetermined calibration function to obtain information including primary material attribute; and
   determining further material attributes of the object by applying a set of functions for an energy band corresponding to the information.

2. The method of claim 1, wherein the information further includes mass thickness information of the object.

3. The method of claim 1, wherein the calibration function is a fitting function of the detection values obtained after the multi-energy radiations interact with a known material.

4. The method of claim 3, wherein a number of multi-energy radiations which are used for fitting the calibration function and interacting with the known material, is equal to or greater than a number of the multi-energy radiations used for interacting with the materials in the object under inspection.

5. The method of claim 1, wherein the multi-energy radiations include radiations having at least three different energy levels or energy spectra.

6. The method of claim 3, wherein the multi-energy radiations include radiations having at least three different energy levels or energy spectra.

7. The method of claim 1, wherein each detection value obtained after the interaction with the object is a transmission intensity obtained after the radiations penetrate the object.

8. The method of claim 3, wherein each detection value obtained after the interaction with the object is a transmission intensity obtained after the radiations penetrate the object.

9. The method of claim 1, wherein the energy band is a specific energy band corresponding to certain material, and in the energy band, the detection values as a result of the interaction between the radiations and the materials have a greater difference when compared to detection values for other materials.

10. The method of claim 1, wherein the set of functions includes functions capable of amplifying a distinction between the detected values of different materials.

11. The method of claim 1, wherein the set of functions includes different function processing models used for segmental processing corresponding to objects having different mass thickness.

12. The method of claim 1, wherein the source of the radiations is a radioactive isotope.

13. The method of claim 1, wherein the source of the radiations is an accelerator.

14. The method of claim 1, wherein the source of the radiations is an X-ray machine.

15. A method for inspecting an object using multi-energy radiations comprising the steps of:
- causing multi-energy radiations to interact with an object under inspection;
- detecting and recording detection values after the interaction between the multi-energy radiations and the object under inspection, and forming images corresponding to the multi-energy radiations;
- substituting a part of the detection values into a predetermined calibration function to determine a mass thickness of the object; and
- selecting weighting factors for the detection values based on the mass thickness to combine the images so as to obtain more accurate gray-scale image.

16. The method of claim 15, further comprising a step of converting the gray-scale image into corresponding color levels in color image.

17. The method of claim 15, wherein the multi-energy radiations include at least two different energy levels or energy spectra.

18. The method of claim 15, wherein determining the mass thickness is based on actual attenuation of the radiations.

19. The method of claim 15, wherein when selecting weighting factors for the detection values, the smaller the mass thickness is, the smaller the weighting factors for the detection values of high-energy radiations are, and the larger the weighting factors for the detection values of low-energy radiations are; while the larger the mass thickness is, the smaller the weighting factors for the detection values of low-energy radiations are, and the larger the weighting factors for the detection values of high-energy radiations are.

20. An apparatus for inspecting an object using multi-energy radiations comprising:
- a radiation source for generating multi-energy radiations which are caused to interact with an object under inspection;
- a detector module array adapted to detect simultaneously multi-energy radiations;
- a processor connected to the detector module array for processing detection values obtained after the interaction between the multi-energy radiations with the object under inspection, said processor having a calibration function for obtaining material attribute and/or for producing gray-scale images of the object; and
- a control system connected to the radiation source for changing operating parameters of the radiation source.

21. The apparatus of claim 20, wherein the multi-energy radiations include radiations having at least three different energy levels or energy spectra.

22. The apparatus of claim 20, wherein the multi-energy radiations include radiations having at least three different energy levels or energy spectra.

23. The apparatus of claim 20, wherein the detector module array is a multi-layered multi-crystal detector compounded of different crystals.

24. The apparatus of claim 23, wherein the different crystals of the detector module array are spaced from each other by filter sheets.

25. The apparatus of claim 21, wherein the radiation source is a radioactive isotope.

26. The apparatus of claim 25, wherein the radiation source is a combination of the radioactive isotopes of different elements, and the multi-energy radiations are generated by making the different radioactive isotopes pass through slots of a collimator in a time series.

27. The apparatus of claim 20, wherein the radiation source is an accelerator capable of emitting radiations having a continuous energy spectrum in which respective energy levels predominate.

28. The apparatus of claim 27, wherein the accelerator includes an energy spectrum modulator for modulating the energy spectrum in front end of the radiation exit.

29. The apparatus of claim 20, wherein the radiation source is an X-ray machine.

30. The apparatus of claim 29, wherein the X-ray machine includes an energy spectrum modulator for modulating the energy spectrum in front end of the radiation exit.

31. The apparatus of claim 28, wherein the energy spectrum modulator has a shape of a wheel, with vanes formed of different modulation materials and rotating around an axis in a time series corresponding to the multi-energy radiations.

32. The apparatus of claim 30, wherein the energy spectrum modulator has a shape of a wheel, with vanes formed of different modulation materials and rotating around an axis in a time series corresponding to the multi-energy radiations.

33. The apparatus of claim 28, wherein the energy spectrum modulator synchronizes the multi-level radiations of the radiation source with signal collection of the detector by transmitting a trigger signal to the control system of the radiation source and a collection signal to a controller of the detector module array.

34. The apparatus of claim 33, wherein the energy spectrum modulator has a shape of a wheel, with vanes formed of different modulation materials and rotating around an axis in a time series corresponding to the multi-energy radiations.

35. The apparatus of claim 33, wherein when receiving the trigger signal, the control system sends immediately to the radiation source signals corresponding to the multi-energy radiations so that the radiation source operates in desirable operating states.

36. The apparatus of claim 20, wherein each detection value of the multi-energy radiations is a transmission intensity obtained after the radiations penetrate through the object under inspection.

* * * * *